(12) United States Patent
Ek et al.

(10) Patent No.: US 11,998,453 B2
(45) Date of Patent: Jun. 4, 2024

(54) DELIVERY SYSTEM FOR ARTICULAR SURFACE IMPLANT

(71) Applicant: ARTHROSURFACE INCORPORATED, Franklin, MA (US)

(72) Inventors: Steven W. Ek, Bolton, MA (US); George Sikora, Bridgewater, MA (US); Timothy Brightman, Franklin, MA (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 131 days.

(21) Appl. No.: 17/518,496

(22) Filed: Nov. 3, 2021

(65) Prior Publication Data
US 2022/0054274 A1 Feb. 24, 2022

Related U.S. Application Data (62) Division of application No. 14/640,667, filed on Mar. 6, 2015, now abandoned.

(60) Provisional application No. 61/950,762, filed on Mar. 10, 2014, provisional application No. 61/949,824, filed on Mar. 7, 2014, provisional application No.
(Continued)

(51) Int. Cl.
*A61F 2/40* (2006.01)
*A61B 17/064* (2006.01)
*A61F 2/28* (2006.01)
*A61F 2/30* (2006.01)
(Continued)

(52) U.S. Cl.
CPC ............ *A61F 2/40* (2013.01); *A61B 17/0642* (2013.01); *A61F 2/28* (2013.01); *A61F 2/30* (2013.01); *A61F 2/30756* (2013.01); *A61F 2/4081* (2013.01); *A61F 2/4606* (2013.01); *A61F 2/4618* (2013.01); *A61F 2/4637* (2013.01); *A61B 2017/0409* (2013.01); *A61B 2017/044* (2013.01); *A61B 2017/0648* (2013.01); *A61F 2002/30331* (2013.01); *A61F 2002/30364* (2013.01); *A61F 2002/30405* (2013.01); *A61F 2002/30462* (2013.01); *A61F 2002/305* (2013.01); *A61F 2002/30649* (2013.01); *A61F 2002/3085* (2013.01);
(Continued)

(58) Field of Classification Search
CPC ...... A61B 2017/0409; A61B 2017/044; A61B 2017/043–0433
See application file for complete search history.

(56) References Cited

U.S. PATENT DOCUMENTS

5,545,180 A * 8/1996 Le ..................... A61L 31/148
                                                          606/232
6,520,964 B2 * 2/2003 Tallarida ............ A61F 2/30756
                                                          623/20.14
(Continued)

*Primary Examiner* — Darwin P Erezo
*Assistant Examiner* — Brigid K Byrd
(74) *Attorney, Agent, or Firm* — Goodwin Procter LLP (57) ABSTRACT

A implant delivery system for securing an implant to an anchor. The implant delivery system includes a driver including a shaft, a biasing body having a first end region configured to engage said driver and a second end region configured to engage a portion of an implant, and a suture extending between the anchor and the shaft of the driver. The driver may be rotated to reduce the length of the suture between the driver and the anchor and generate a biasing force urging the implant into engagement with the anchor. The biasing force is substantially not transmitted to the bone.

10 Claims, 11 Drawing Sheets

Related U.S. Application Data

61/949,789, filed on Mar. 7, 2014, provisional application No. 61/949,774, filed on Mar. 7, 2014.

(51) Int. Cl.
*A61F 2/46* (2006.01)
*A61B 17/04* (2006.01)

(52) U.S. Cl.
CPC ............ *A61F 2002/4627* (2013.01); *A61F 2002/4628* (2013.01); *A61F 2310/00011* (2013.01)

(56) References Cited

U.S. PATENT DOCUMENTS

| | | | | |
|---|---|---|---|---|
| 2007/0167950 A1* | 7/2007 | Tauro | ............... | A61B 17/0487 |
| | | | | 606/232 |
| 2009/0018581 A1* | 1/2009 | Anderson | .......... | A61B 17/0401 |
| | | | | 606/232 |
| 2010/0198258 A1* | 8/2010 | Heaven | ............. | A61B 17/0401 |
| | | | | 606/232 |

\* cited by examiner

DELIVERY SYSTEM FOR ARTICULAR SURFACE IMPLANT

CROSS REFERENCE TO RELATED APPLICATIONS

This application is a Divisional of U.S. application Ser. No. 14/640,667 filed Mar. 6, 2015, which claims the benefit of U.S. Provisional Application Ser. No. 61/949,774, filed Mar. 7, 2014; U.S. Provisional Application Ser. No. 61/949,789, filed Mar. 7, 2014; U.S. Provisional Application Ser. No. 61/949,824, filed Mar. 7, 2014; and U.S. Provisional Application Ser. No. 61/950,762, filed Mar. 10, 2014, the entire disclosures of which are fully incorporated herein by reference.

FIELD

The present disclosure relates to delivery systems for bone implants, and more particularly, to delivery systems for articular surface implants.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. One method of installing an implant involves applying a blunt force, e.g., a hammer/mallet or the like, to the implant. Unfortunately, some of the blunt force is transmitted from the implant into the surrounding bone and/or tissue and can cause damage to the bone/tissue. This is particularly problematic in small bones (such as, but not limited to, bones in the hand and/or foot) as well as patients who suffer from reduced bone mass and density that can lead to fracture (such as, but not limited to, osteoporosis or the like).

BRIEF DESCRIPTION OF THE DRAWINGS

Features and advantages of the claimed subject matter will be apparent from the following detailed description of some example embodiments consistent therewith, which description should be considered with reference to the accompanying drawings, wherein:

Although the following Detailed Description will proceed with reference being made to some illustrative example embodiments, many alternatives, modifications, and variations thereof will be apparent to those skilled in the art.

DETAILED DESCRIPTION

Generally, the present disclosure may feature systems, devices and/or methods for installing an implant anchor and/or delivering and attaching an implant to the anchor. By way of a general overview, one embodiment of the present disclosure may feature an implant delivery system for use with an implant system having an anchor and an implant (e.g., implant body) configured to be secured thereto. The implant delivery system may be used to facilitate delivering (e.g., securing) the anchor to the bone beneath a patient's articular surface and/or to couple, mount, or otherwise secure the implant body to the anchor. For example, the implant delivery system may be configured to generate sufficient force to allow the implant body to be secured to the anchor without applying any force to the surrounding bone or tissue. More specifically, the implant delivery system may generate and apply a biasing force against the implant and the anchor which urges the implant body into engagement with the anchor, thereby securing the implant body to the anchor without applying any force to the surrounding bone. The biasing force generated by the implant delivery system may therefore be applied only to the implant system, and not the surrounding bone or tissue.

Because the biasing force is not transmitted/applied into the surrounding bone or tissue, the implant delivery system may reduce, minimize, and/or eliminate damage to the surrounding bone while securing the implant body to the anchor, thereby allowing the implant delivery system to be used with small bones (such as, but not limited to, phalange bones and/or metatarsal bones in the foot and/or hands) as well with patients who suffer from reduced bone mass and density that can lead to fracture (such as, but not limited to, osteoporosis or the like). Additionally, because the implant delivery system is capable of generating high biasing forces without transmitting/applying the biasing force to the surrounding bone or tissue, the connection between the implant body and the anchor may be stronger and more robust, thereby increasing the life expectancy of the implant system.

Figure 1:
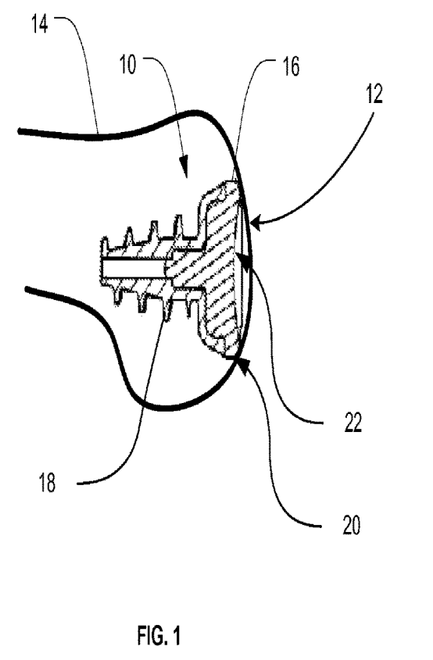
FIG. 1 generally illustrates a cross-sectional view of one embodiment of an implant system consistent with the present disclosure secured within an excision site in a bone.
Figure 2:
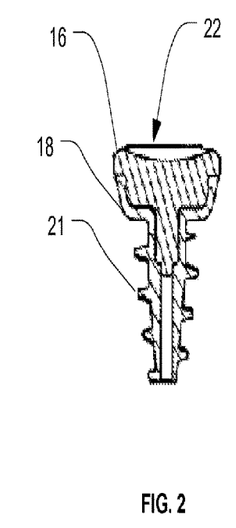
FIG. 2 generally illustrates a cross-sectional view of one embodiment of an assembled implant system consistent with the present disclosure.
Figure 3:
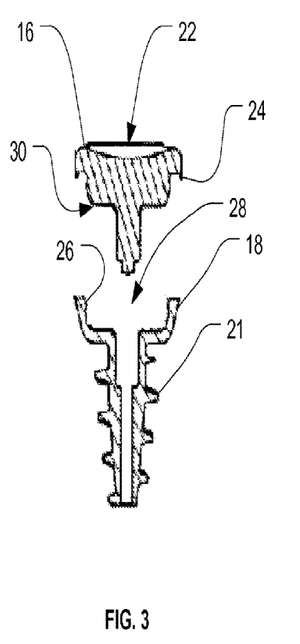
FIG. 3 generally illustrates a cross-sectional view of one embodiment of an unassembled implant system consistent with the present disclosure.

Turning now to FIGS. 1-3, one embodiment of an implant system 10 which may be used with an implant delivery system consistent with the present disclosure is generally illustrated. In particular, FIG. 1 generally illustrates the implant system 10 installed in the articular surface 12 of a patient's bone 14, FIG. 2 generally illustrates an assembled implant system 10, and FIG. 3 generally illustrates an exploded, unassembled implant system 10 consistent with the present disclosure. The implant system 10 may generally include an implant (e.g., implant body) 16 configured to be secured to an anchor 18. The anchor 18 is configured to be secured to the bone 14 within an excision site 20 formed beneath the patient's articular surface 12 such that a load bearing surface 22 of the implant 16 is generally flush with the patient's surrounding articular surface 12 as generally illustrated in FIG. 1. The excision site 20 may be formed using any method and system known to those skilled in the art, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. According to one embodiment, the anchor 18 may be secured to the bone 14, for example, using one or more external threads, ribs, protrusions, bone cement, barbs, grooves or any other structure 21 that enables the anchor 18 to be secured to the bone 14. The use of threads 21 as generally illustrated may advantageously allow the height of the implant 12 to be adjusted by rotating the anchor 18 within the bone 14 such that the implant 16 is flush with the surrounding articular surface 12.

It should be appreciated that the implant system 10 illustrated is provided for illustrative purposes, and that the implant delivery system may be used with any multi-piece implant having an anchor that is coupled (either directly or indirectly) to an implant/implant body. For example, the implant delivery system may be used with implant systems for replacing any articular surface such as, but not limited to, shoulder joints (e.g., but not limited to, the glenohumeral joint), hip joint (e.g, but not limited to, the acetabulofemoral joint), foot and/or hand joints (e.g., but not limited to, metacarpophalangeal joints, metatarsophalangeal joints, and/or interphalangeal joints), or the like. The implant systems may include total joint implants (wherein all or substantially all of the articular surface of at least one bone is replaced with the artificial surface of the implant) and/or partial implants (wherein substantially only the damaged portion(s) of the articular surface of a bone is replaced with the artificial surface of the implant). The implant delivery system may also be used to secure together a multi-piece pin or rod in a bone to facilitate healing of a fracture or broken bone.

As discussed above, the implant 16 may be secured to the anchor 18 by way of a connection. For example, the implant 16 may include at least one first fixation element 24 configured to engage with at least one second fixation element 26 of the anchor 18 to secure the implant 16 to the anchor 18. According to one embodiment, the first and the second fixation elements 24, 26 may include one or more recesses, groves, slots or the like configured to corresponding to one or more protrusions, ribs, barbs, or the like, for example, in a snap-fit arrangement in which the first and/or second fixation elements resiliently deflect. The first and second fixation elements 24, 26 may be disposed about the entire perimeter/periphery of the implant 16 and anchor 18, and/or about one or more regions of the perimeter/periphery. The first and second fixation elements 24, 26 may prevent the implant 16 from becoming free relative to the anchor 18 (for example, to prevent axial and/or rotational movement of the implant 16 relative to the anchor 18). Optionally, the implant 16 may be at least partially received in an implant cavity 28 formed in the anchor 18 such that a bone facing surface 30 of the implant 16 engages against at least a portion of the implant cavity 28, thereby preventing the implant 16 from moving distally when a force is applied to the load bearing surface 22.

It should be appreciated that while the first and second fixation elements 24, 26 are generally illustrated as a recess and a protrusion, respectively, the implant system 10 consistent with the present disclosure is not limited to this arrangement unless specifically claimed as such. For example, the first and second fixation elements 24, 26 may include a protrusion and a recess, respectively, as well as other embodiments. Additionally, the anchor 18 may optionally include a passageway 32, for example, a longitudinal passageway, configured to be advanced over a guide wire (not shown) as generally described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. For example, the anchor 18 may be inserted into bone 14 or may be inserted into a shaft drilled in the bone 14 to reduce risks or complications arising from the insertion of the anchor 18. Without limitation, a pilot hole may be formed in the bone 14 for receiving the anchor 18 prior to installing the anchor 18. A diameter of the pilot hole may be smaller than the anchor 18, although example embodiments may vary and are not limited thereto.

It may be appreciated that the strength or ruggedness of the snap-fit connection between the implant 16 and the anchor 18 may depend on the selected materials (e.g., the rigidity) and size/dimensions. In general, more rigid (i.e., less deformable) materials and/or larger sizes/dimensions will result in a stronger, more robust connection between the implant 16 and the anchor 18. While a stronger and more robust connection between the implant 16 and the anchor 18 is generally desirable, the resulting force necessary to make the snap-fit connection increases.

Traditionally, the force necessary to secure the implant 16 to the anchor 18 has been generated using a blunt force, e.g., a hammer/mallet or the like. More specifically, with the anchor 18 secured in the bone 14, the surgeon attempts to align the implant 16 relative to the anchor 18 and impacts the implant 16 with the hammer/mallet to force the implant 16 into engagement with the anchor 18. As may be appreciated, however, a substantial amount of force is also applied to the surrounding bone 14, and if the force applied to the bone 14 is too great, the bone 14 may be damaged. Consequently, the strength of the connection between the implant 16 and the anchor 18 may be limited in many applications (e.g., but not limited to, small bones in the hand and foot as well as implant system 10 installed proximate to the perimeter of a bone) by the strength of the surrounding bone 14. Additionally, it may be very difficult for the surgeon to properly align the implant 16 with respect to the anchor 18.

As discussed herein, the implant delivery system consistent with one embodiment of the present disclosure solves this problem by generating a biasing force to secure the implant 16 to the anchor 18 wherein the biasing force is only applied against the implant 16 and the anchor 18. The biasing force generated by the implant delivery system may therefore be applied only to the implant system 10, and not the surrounding bone or tissue 14. An implant delivery system consistent with the present disclosure may also be used to facilitate securing the anchor 18 into the bone 14. Features and aspects of an implant delivery system consistent with the present disclosure will generally be described.

Turning now to FIGS. 4-12, systems and methods for securing an anchor 18 into the bone and securing the implant 16 to the anchor 18 using an implant delivery system 100 consistent with the present disclosure are generally illustrated. In a first mode (as generally illustrated in FIGS. 4-8), the implant delivery system 100 may be used to secure the anchor 18 into an excision site formed in the bone. In a second mode (FIGS. 9-12), the delivery system 100 may be used to secure the implant 16 to the anchor 18 to assemble the implant system 10 within the excision site. As may be appreciated, the implant delivery system 100 may be used with any implant system 10 described herein and is not limited to the illustrated implant system 10 unless specifically claimed as such.

Figure 5:
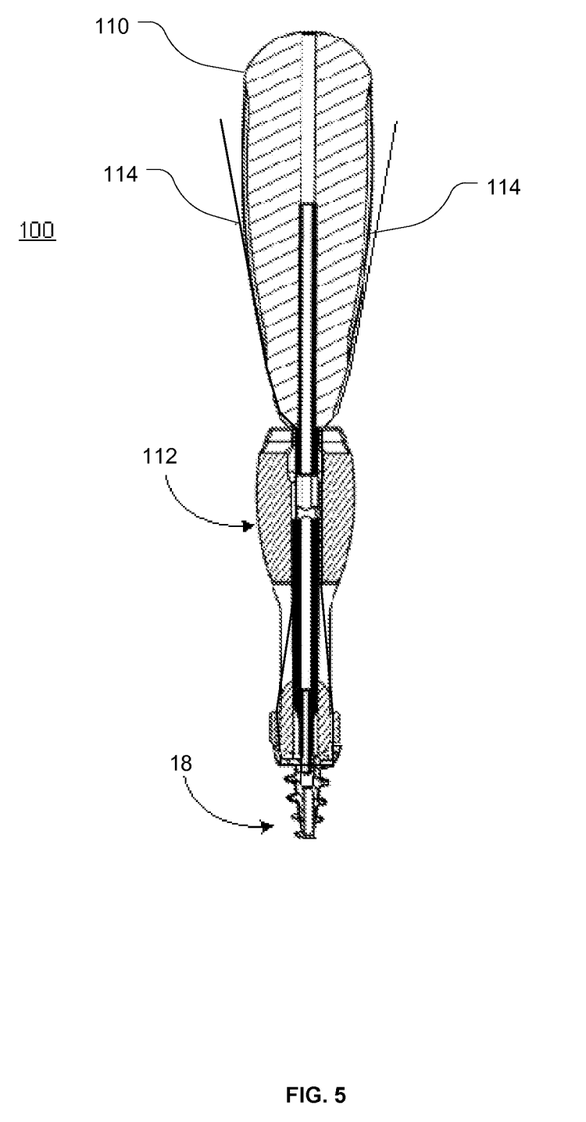
FIG. 5 generally illustrates an assembled, cross-sectional view of one embodiment of an implant delivery system consistent with the present disclosure.
Figure 6:
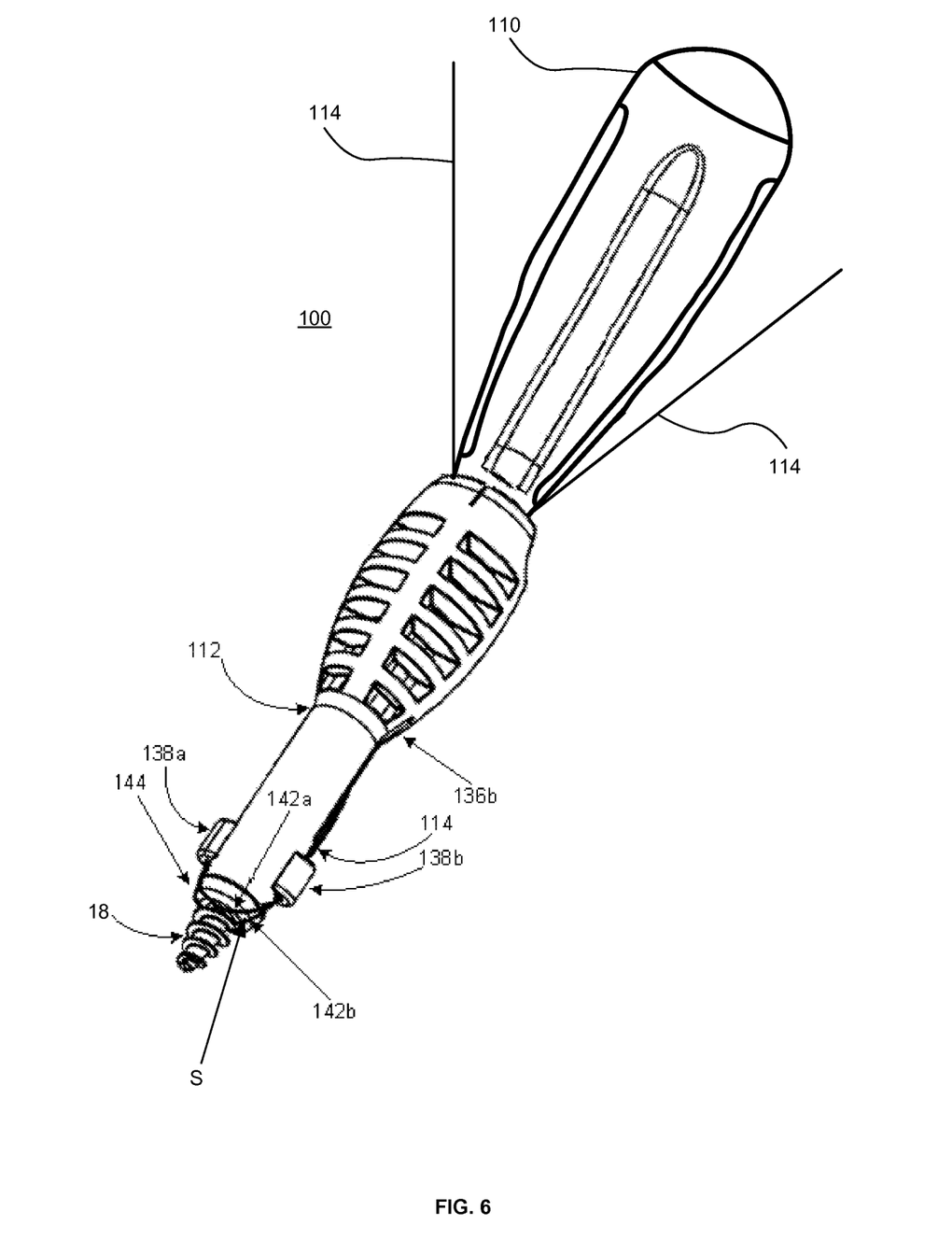
FIG. 6 generally illustrates an assembled, perspective view of one embodiment of an implant delivery system consistent with the present disclosure.
Figure 7:
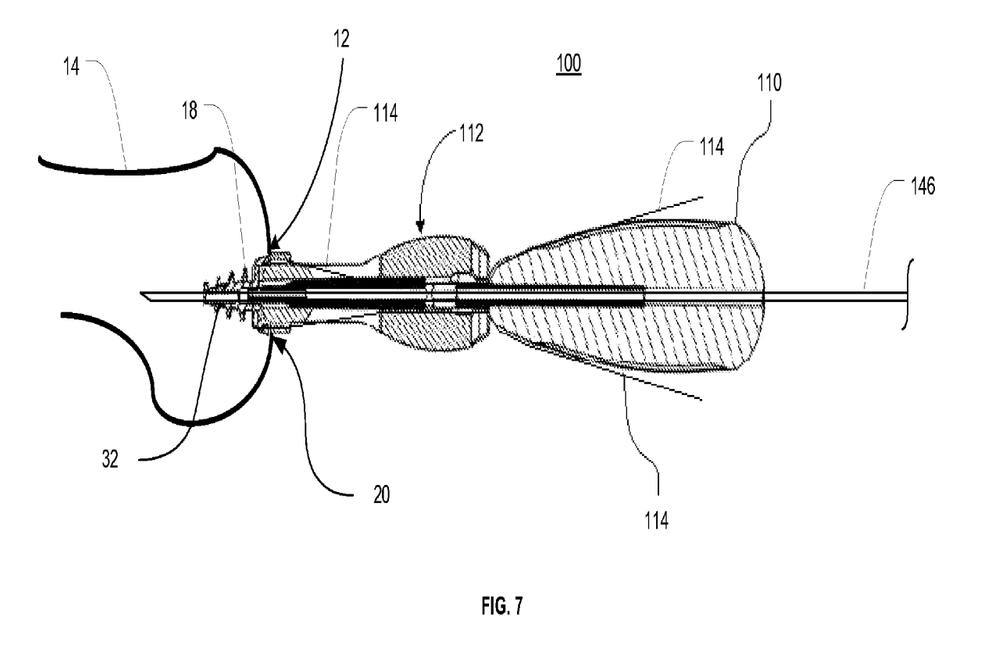
FIG. 7 generally illustrates a cross-sectional view of one embodiment of an implant delivery system securing an anchor within an excision site in a bone consistent with the present disclosure.
Figure 8:
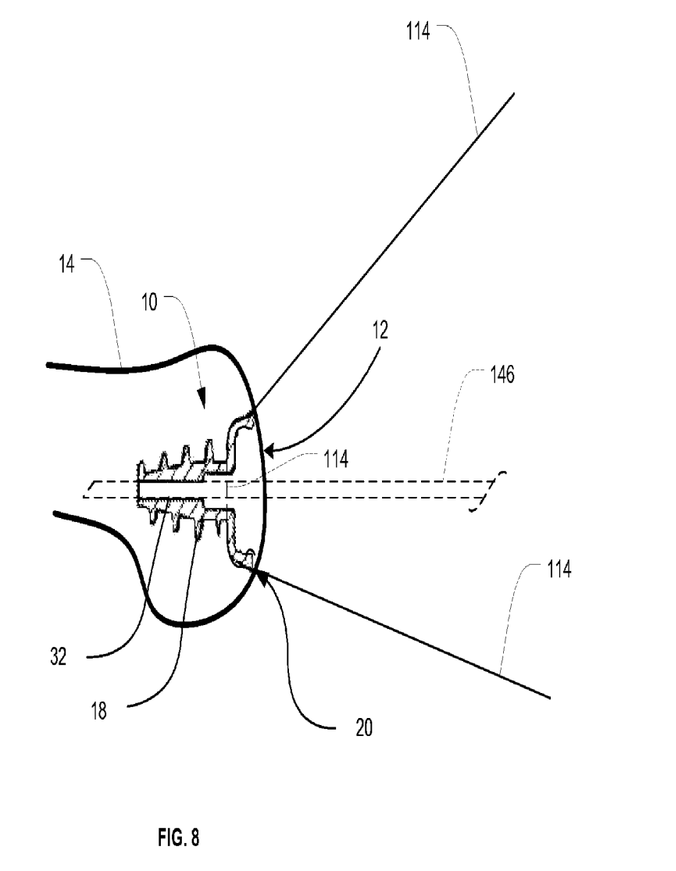
FIG. 8 generally illustrates a cross-sectional view of an anchor secured within an excision site in a bone consistent with the present disclosure.

With reference to FIGS. 4-8, one embodiment of system and method for using the implant delivery system 100 to secure the anchor 18 to bone within an excision site is generally illustrated. The implant delivery system 100 may include a driver 110, a biasing body 112, and at least one suture 114. As explained herein, the implant delivery system 100 may be configured to retain the anchor 18 into engagement with the driver 110 and to secure the anchor 18 to bone 14 within an excision site 20 (as generally illustrated in FIGS. 7 and 8). For example, the driver 110 may be received through the biasing body 112, and the suture 114 may be disposed around a portion of the anchor 18 to provide increased control and/or maintain contact between the driver 110 and the anchor 18 while securing the anchor 18 into the bone 14 within the excision site 20. The excision site 20 may be formed using any method and system known to those skilled in the art.

Figure 4A:
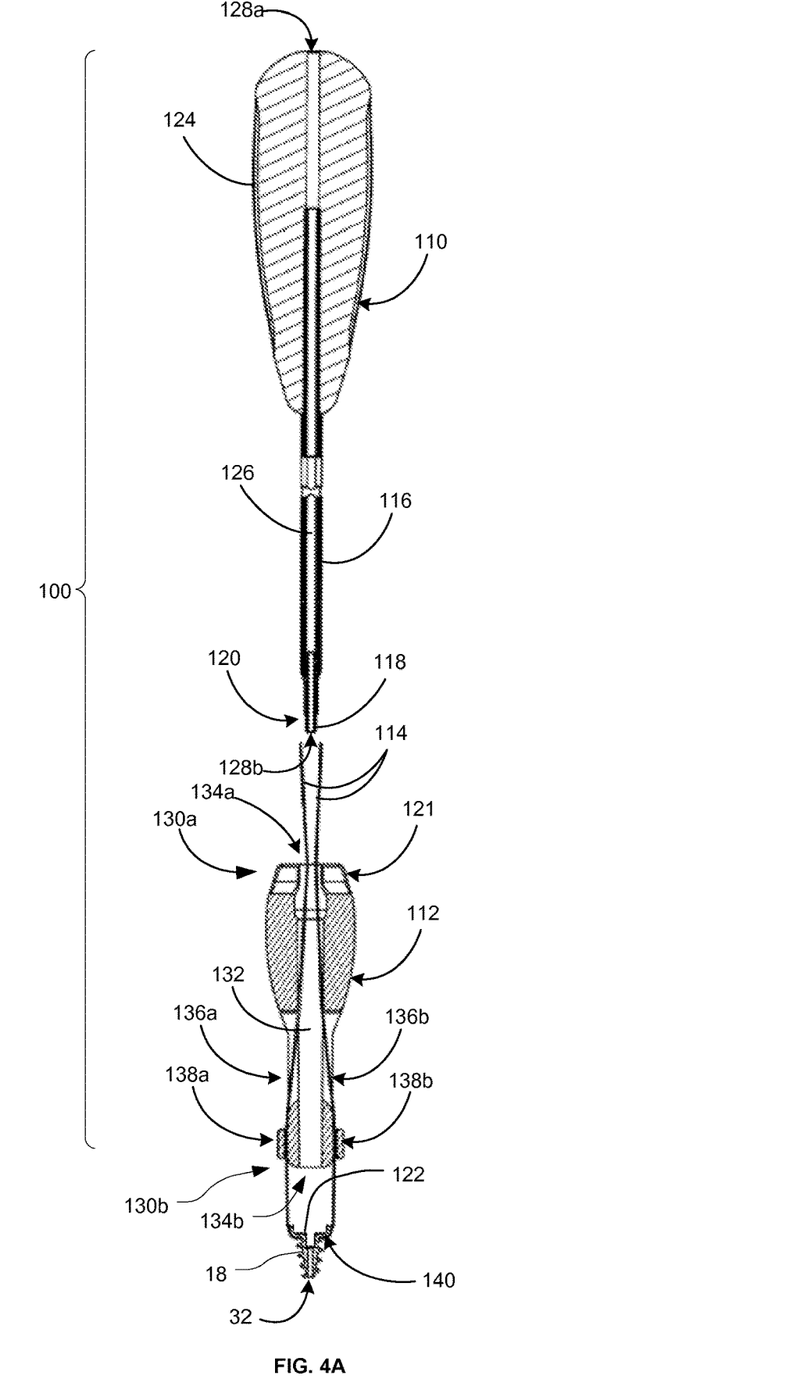
FIG. 4A generally illustrates an exploded, cross-sectional view of one embodiment of an implant delivery system consistent with the present disclosure.
Figure 4B:
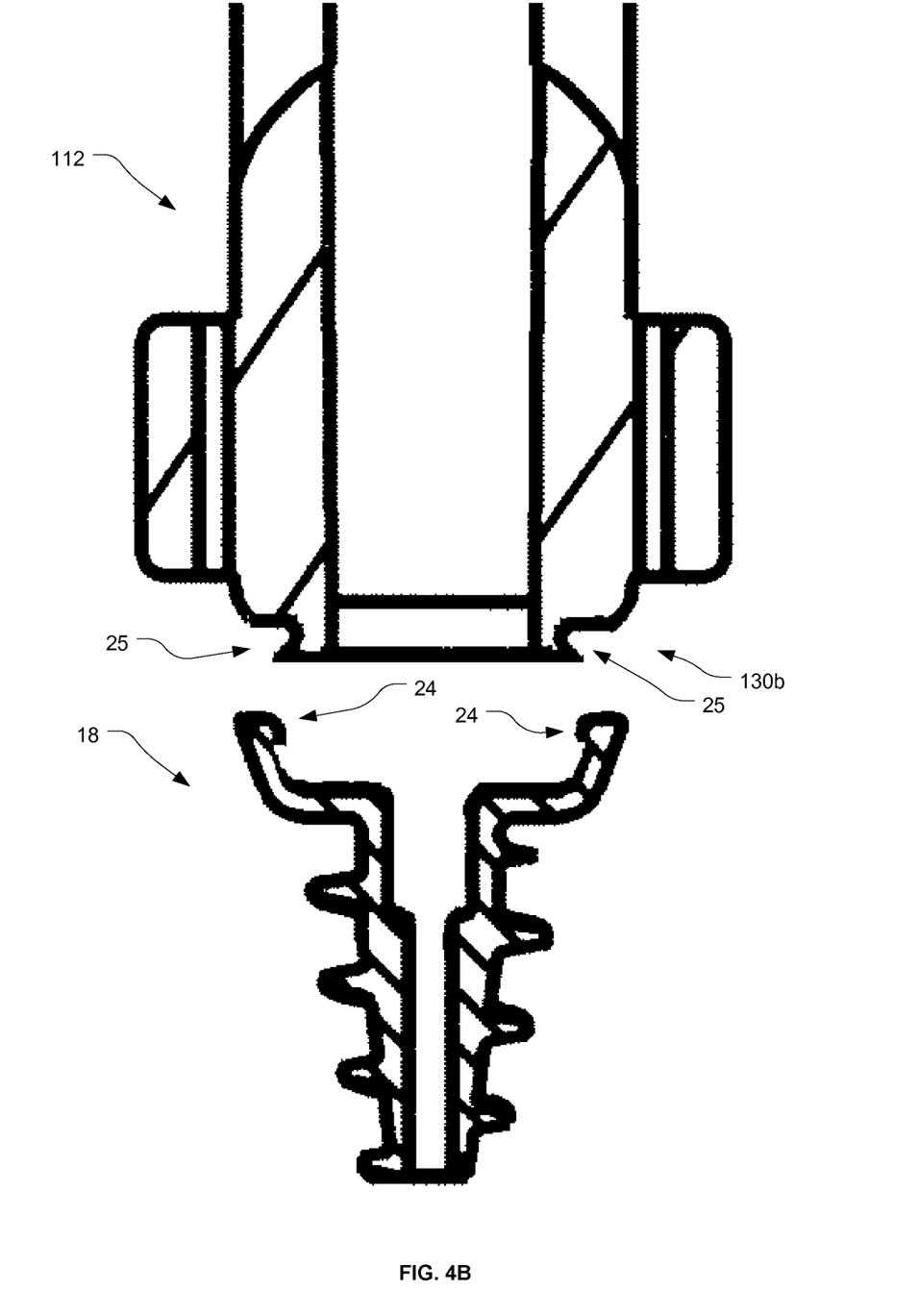
FIG. 4B generally illustrates a partial view of another embodiment of an implant delivery system consistent with the present disclosure.

The driver 110, FIG. 4A, includes a longitudinally disposed shaft 116 having an engagement portion 118 disposed about a distal end 120. The engagement portion 118 is configured to be coupled with a corresponding engagement portion 122 of the anchor 18 and to transmit torque as generally illustrated in FIGS. 5-7. For example, the engagement portion 118 may be a male-shaped coupling unit (such as, but not limited to, a splined or hex-shaped driver) configured to couple with a female-shaped coupling unit 122 (such as, but not limited to, a splined or hex-shaped recession formed in the anchor 18) in order to rotate or drive the anchor 18 into the bone. However, the engagement portions 118, 122 may vary and are not limited thereto. For example, the driver 110 may be configured to accept interchangeable bits having a different engagement portion 118 configurations, thereby allowing the engagement portion 118 of the driver 110 to be coupled to the engaging portion 122 of the anchor 18 using several different bits as necessary. Alternatively (or additionally), the engagement portion 118 may have a female-shaped coupling unit and the anchor 18 may have a male-shaped coupling unit. The shape of the engaging portions 118, 122 may be other than splined or hexagonal, and those in the art will recognize that one of any number of shapes or configuration for such components may be employed in a device or method consistent with example embodiments. Optionally, the engagement portion 118 may be magnetized or otherwise configured to maintain contact or control over the anchor 18.

While the engaging portion 122 of the anchor 18 is shown located on an inner wall of the narrow portion of the anchor 18, example embodiments may vary and are not limited thereto. For example, the engaging portion 122 of the anchor 18 may be located on an inner wall of the wide portion of the anchor 18 and/or on an outer wall of either the narrow portion or the wide portion of the anchor 18. Optionally, an intermediate or adapting portion (not shown) may be used to connect the driver 110 to the anchor 18.

The driver 110 may optionally include a handle 124. The handle 124 may facilitate grasping of the driver 110 and may be configured to cause a rotational force or a torque on the shaft 116, which may ultimately impart a rotational force or torque on the anchor 18 to secure the anchor 18 into the bone. The handle 124 may be separate from the shaft 116 (either permanently or removably coupled thereto), or may be a unitary, single piece with the shaft 116. While the handle 124 is illustrated as having a larger width than the shaft 116, example embodiments may vary and are not limited thereto. For example, the handle 124 may include a lever arm or may be configured to couple to a lever arm that is used to create the rotational force or torque.

The handle 124 and/or the shaft 116 may be cannulated to define a longitudinal passageway 126. The longitudinal passageway 126 may include proximal and distal openings 128a, 128b configured to be advanced over a guide wire (not shown for clarity), for example, when securing the anchor 18 into the bone within the excision site.

The biasing body 112 defines a shaft passageway 132 extending between a first and a second end region 130a, 130b having a first and second opening 134a, 134b. The shaft passageway 132 is configured to receive at least a portion of the shaft 116 of the driver 110, for example, as generally illustrated in FIGS. 5 and 6. The shaft 116 and the shaft passageway 132 may be configured such that the distal end 120 of the shaft 116 extends beyond the second end 134b of the shaft passageway 132 to allow the engagement portion 118 of the driver 110 to engage the corresponding engagement portion 122 of the anchor 18, for example, as generally illustrated in FIGS. 5 and 6. Optionally, the biasing body 112 may include a driver cradle 121, discussed in greater detail herein, which may be used to secure the implant 16 (not shown) with the anchor 18.

Additionally, the second end region 130b may include a fixation element 25 (FIG. 4B) which substantially corresponds to the first fixation element 24 of the implant 16. In this manner, the fixation element 25 of the second end region 130b of the biasing body 112 may be coupled to the second fixation element 26 of the anchor 18 to generally secure the anchor 18 to the biasing body 112. The connection between the biasing body 112 and the anchor 18 may facilitate placement of the anchor 18 within the excision site by creating a generally secure connection therebetween. It may be appreciated, however, that the connection between the fixation element 25 of the second end region 130b and the second fixation element 26 of the anchor 18 does not need to be as strong as the connection between the first and second fixation elements 24, 26 since it is only generally intended to help advance the anchor 18 to and align the anchor 18 within the excision site.

Alternatively (or in addition to), the biasing body 112, FIG. 4A, may be configured to receive a suture 114 disposed around (e.g., wrap around) a portion of the anchor 18. Tension may be applied to the suture 114 to generally urge the anchor 18 into contact with the driver 110 and/or the biasing body 112 to provide more control over and/or maintain contact between the driver 110 and the anchor 18.

The suture 114 may be configured to extend through and/or around the biasing body 112 in any manner known to those skilled in the art. For example, the suture 114 may extend through the first opening 134a of the shaft passageway 132 of the biasing body 112, out through one or more suture apertures/openings/passageways 136a, 136b, through one or more suture alignment guides 138a, 138b and around a contact portion 140 of the anchor 18. The suture passageways 136a, 136b may allow the suture 114 to pass from the exterior of the biasing body 112 to the interior of the shaft passageway 132. While the suture passageways 136a, 136b are illustrated in the middle of the biasing body 112, example embodiments may vary and are not limited thereto. It should also be appreciated that the suture 114 does not have to pass through the shaft passageway 132, and instead the biasing body 112 may include one or more separate passageways (not shown) for the suture 114.

The suture alignment guides 138a, 138b are configured to retain the suture 114 about the distal end of the biasing body 112. According to one embodiment, the suture 114 may include a first and a second portion 142a, 142b (best seen in FIG. 6) which form a basket, cradle, or frame 144 extending about the contact portion of the anchor 18. The first and second portions 142a, 142b may be formed from two or more pieces of suture, or may be formed from a single piece of suture. The suture alignment guides 138a, 138b may be configured to prevent the first and second portions 142a, 142b of the cradle 144 from slipping off the anchor 18 by restricting the separation angle S of the first and second portions 142a, 142b of the cradle 144.

While the suture alignment guides 138a, 138b are shown at the distal end of the biasing body 112 nearest the anchor 18, example embodiments may vary and are not limited thereto. For example, the suture alignment guides 138a, 138b may be located anywhere along the biasing body 112 provided the suture alignment guides 138a, 138b may prevent the suture 114 from slipping off the anchor 18. Additionally, while the suture alignment guides 138a, 138b are shown as an exterior protrusion of the biasing body 112 with holes to allow the suture 114 to pass through, example embodiments may vary and are not limited thereto. For example, the suture alignment guides 138a, 138b may be flush with the biasing body 112 or may protrude in an arc shape, with a gap between one edge of the suture alignment guides 138a, 138b and the biasing body 112 to allow the suture 114 to enter. It may also be appreciated that the length of the suture alignment guides 138a, 138b may vary and the suture alignment guides 138a, 138b may be integrated into the suture passageways 136a, 136b.

While the contact portion 140 of the anchor 18 is shown on the bottom edge of the anchor 18, example embodiments may vary and the contact portion 140 may be situated anywhere along the anchor 18. For example, the contact portion 140 may also be disposed about the top portion of anchor 18. The contact portion 140 of the anchor 18 may include a flat edge or may include guides, grooves, slots, or channels configured to receive the suture 114. For example, the suture 114 may extend through a passageway formed in the anchor 18 such that a portion of the anchor 18 generally surrounds the suture 114, and the cradle 144 may be eliminated.

To secure the anchor 18 to the bone 14 within the excision site 20, the suture 114 may be received through the biasing body 112 (e.g., through the first opening 134a of the shaft passageway 132, out through the suture passageways 136a, 136b, and through the suture alignment guides 138a, 138b) such that the cradle 144 is disposed about the contact portion 140 of the anchor 18 as generally illustrated in FIG. 4A. The driver 110 may be advanced through shaft passageway 132 until the engagement portion 118 contacts the corresponding engagement portion 122 of the anchor 18. The suture 114 may then be tensioned to retain the engagement between the driver 110 and the anchor 18, for example, by applying a force against the suture 114 in a direction generally away from the anchor 18 as generally illustrated in FIGS. 5 and 6. Alternatively (or in addition), the fixation element 25 (FIG. 4B) of the biasing body 112 may be secured to the fixation element 26 of the anchor 18, and the driver 110 may engage the anchor 18 as described herein.

With the anchor 18 securely engaged with the driver 110, the anchor 18 may be advanced to and aligned with the excision site 20 (as generally illustrated in FIG. 7) formed in the patient's articular surface 12 and bone 14. Optionally, the anchor 18 may be aligned with the excision site 20 using a guide wire 146 extending outwardly from the bone 14 within the excision site 20. Because the anchor 18 is retained against the driver 110, it is easier for the surgeon to align the anchor 18 relative to the excision site 20. As discussed herein, the anchor 18 may optionally include a cannulated passageway 32 (best seen in FIG. 4A) that is generally aligned with (e.g., generally co-axial) the longitudinal passageway 126 of the driver 110 (as best illustrated in FIG. 7) such that the anchor 18 and the driver 110 (and optionally the biasing device 112) may be advanced over the guide wire 146. The optionally use of the cannulated passageway 32 and the guide wire 146 may further aid in aligning the anchor 18 at the desired angle with respect to the excision site 20 and the surrounding articular surface 12.

Once the anchor 18 is aligned with respect to the excision site 20, the driver 110 may then be used to secure the anchor 18 into the bone 14, for example, by rotating the driver 110, thereby causing the anchor 18 to rotate. The height of the anchor 18 may be verified using a trial gauge (not shown) which may be easily inserted/placed into the anchor 18 to ensure that the implant 16 (e.g., FIG. 1) is substantially flush with the surrounding articular surface 21. Once the height of the anchor 18 is verified, the driver 110 (and optionally the biasing device 112 and/or the guide wire 146) may be removed, leaving the anchor 18 (and optionally the suture 114) remaining in the bone 14, as generally illustrated in FIG. 8. While the anchor 18 is illustrated having threads 21, it may be appreciated that the anchor 18 may be secured to the bone 14 using any device(s) known to those skill in the art including, but not limited to, ribs, barbs, bone cement, porous structures, and the like.

It should also be appreciated that the biasing device 112 does not have to be used when advancing and/or aligning the anchor 18 with respect the excision site 20. For example, the biasing device 112 may be eliminated and tension may be applied to the suture 114 to keep the anchor 18 engaged with the driver 110. Alternatively, the anchor 18 may be advanced to and aligned with the excision site 20 without using the driver 110. For example, the suture 114 may be secured about a portion of the anchor 18, and once the anchor 18 is aligned within the excision site 20, the driver 110 may engage the anchor 18 and used to secure the anchor 18 within the excision site 20 in the bone 14.

Turning now to FIGS. 9-12, systems and methods for securing an implant 16 to the anchor 18 using an implant delivery system 100 consistent with the present disclosure are generally illustrated. As discussed herein, the implant delivery system 100 may be configured to generate a biasing force to secure the implant 16 to the anchor 18 wherein the biasing force is only applied against the implant 16 and the anchor 18, and not the surrounding bone or tissue 14.

Figure 9:
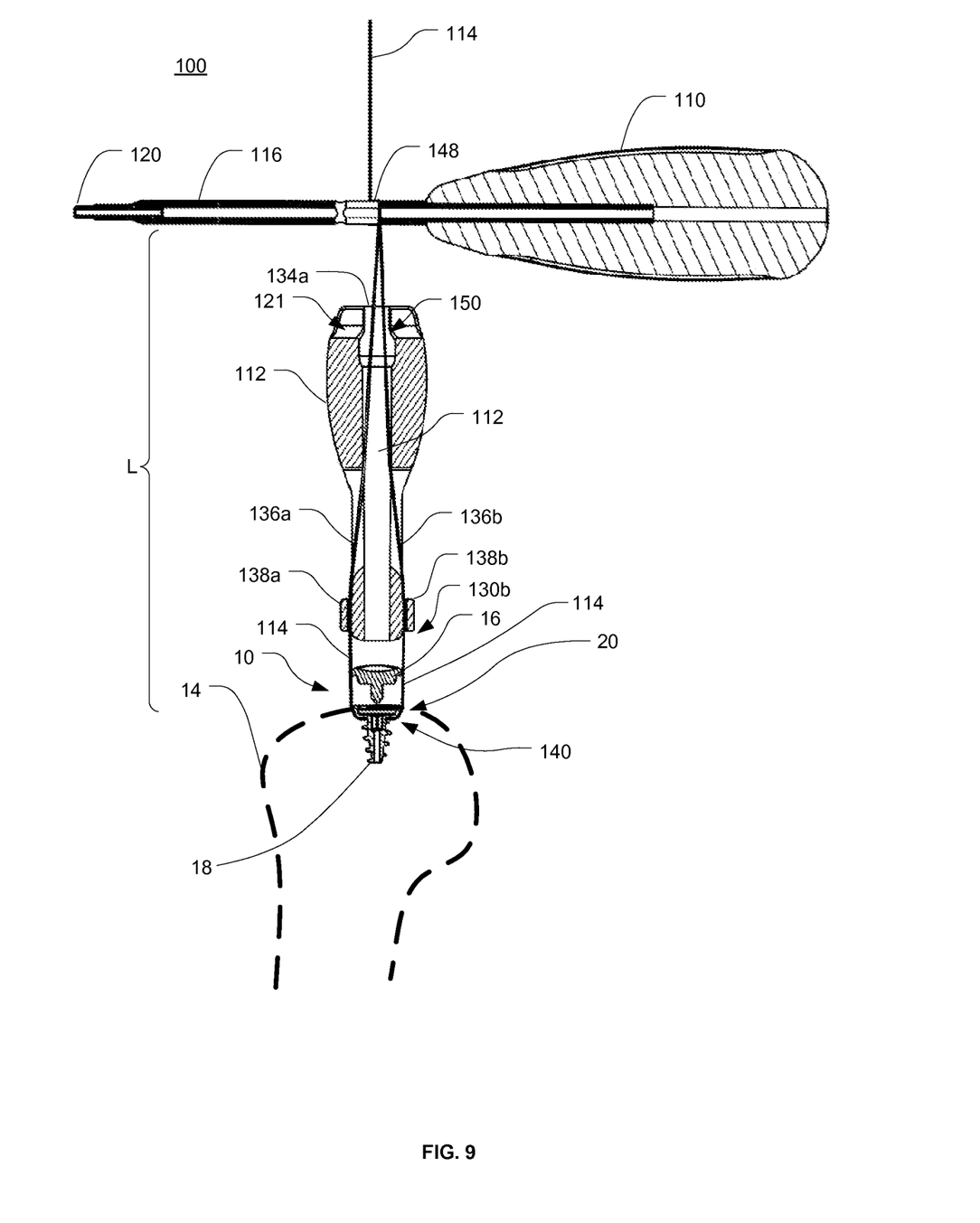
FIG. 9 generally illustrates a cross-sectional view of an implant delivery system securing an implant to an anchor consistent with the present disclosure.
Figure 10:
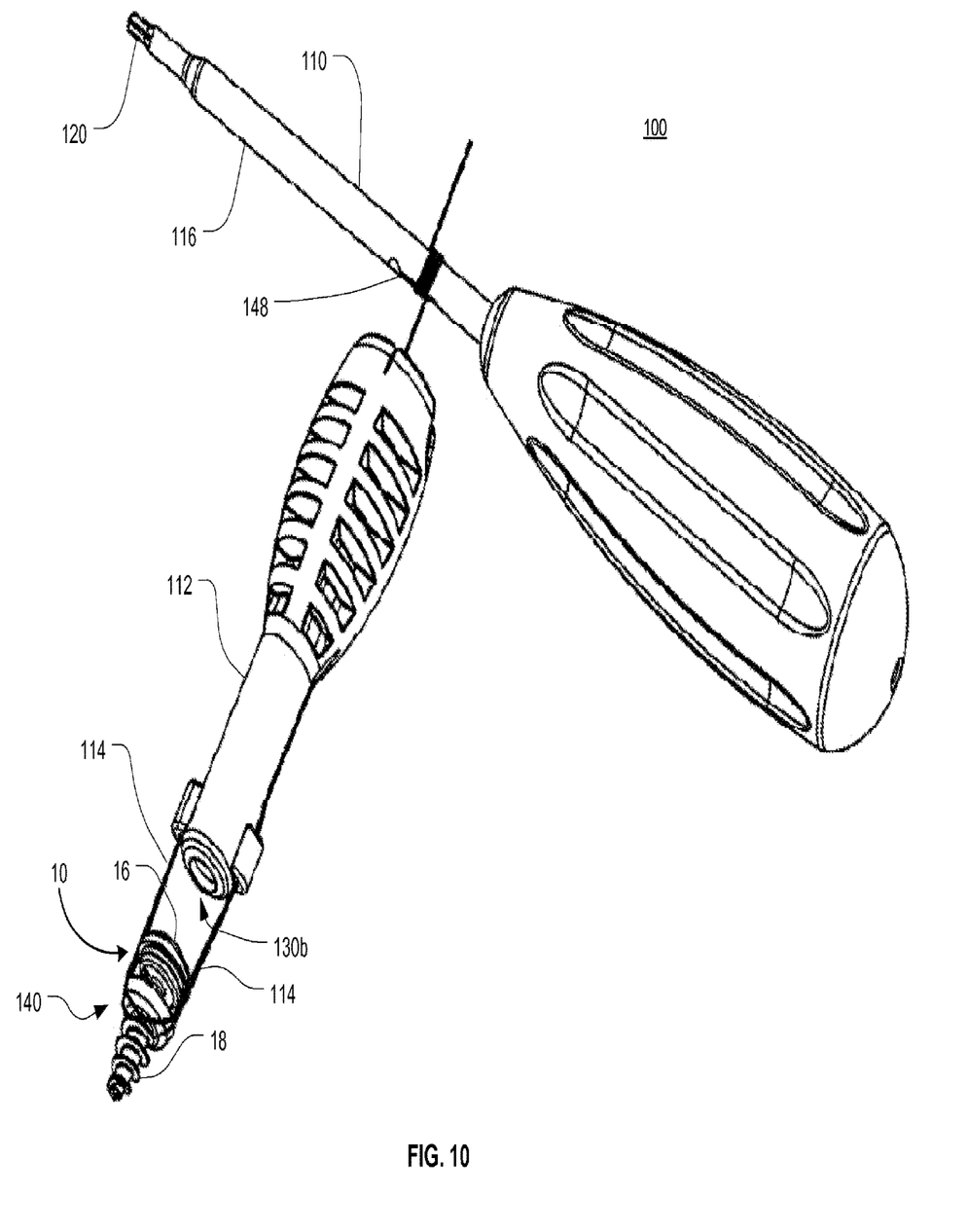
FIG. 10 generally illustrates a perspective view of an implant delivery system for securing an implant to an anchor consistent with the present disclosure.

With the anchor 18 secured to the bone 14 and the suture 114 disposed about the contact portion 140 of the anchor 18 as described herein, the implant 16 may be arranged (i.e., placed) between the anchor 18 and the second end region 130b of the biasing device 112 as generally illustrated in FIGS. 9 and 10. The suture 114 may extend around the contact portion 140 of the anchor 18, through suture alignment guides 138a, 138b and suture passageways 136a, 136b, and exit through the first opening 134a of the shaft passageway 132 of the biasing body 112. The suture 114 may also be generally coupled or secured to a portion of the driver 110, for example, a portion of the shaft 116. For example, the driver 110 may include a suture engagement 148 configured to allow the suture 114 to be generally fixed or retained by the driver 110.

According to one embodiment, the suture engagement 148 may include a hole or aperture through the shaft 116. At least a portion of the suture 114 may pass through the hole 148, and the suture 114 may be secured within the suture engagement 148 as the driver 110 is rotated to reduce the length L of the suture 114 between the driver 110 and the anchor 18 as explained herein. It should be appreciated that the suture engagement 148 may include any device for generally securing the suture 114 to the driver 110. For example, the suture engagement 148 may include an external protrusion, a groove, non-cylindrical region, and/or a slot configured to secure the suture 114. Alternatively, the suture 114 may be wrapped around the shaft 116, and the tension generated by the rotation of the driver 110 may secure the suture 114 thereto. The length of the biasing body 112 may be selected to allow the surgeon sufficient room to rotate the driver 110, and therefore may depend on the intended application.

With the suture 114 generally secured to the driver 110, the driver 110 may be rotated about its longitudinal axis A as it is received within the driver cradle 121. The driver cradle 121 may be configured to receive the driver 110 (e.g., the shaft 116) and generally retain the shaft 116 as the shaft 116 is rotated relative to the biasing body 112. For example, the driver cradle 121 may include one or ore recesses, grooves, or lips formed in the first end region 134a of the biasing body 112. The driver cradle 121 may also include one or more holes or passageways formed through the biasing body 112 configured to receive and generally retain the shaft 116.

Optionally, the driver cradle 121 may include an enlarged opening 150 (best seen in FIG. 9). As the driver 110 is rotated, the suture 114 begins to wrap around the shaft 116, thereby increasing the diameter of the shaft 116. The enlarged opening 150 provides a void space that the suture 114 can pass through as the driver 110 is rotated and the suture 114 builds up around the shaft 116. As a result, the suture 114 may generally avoid contact with the driver cradle 121, and the torque necessary to rotate the driver 110 may be reduced.

Figure 11:
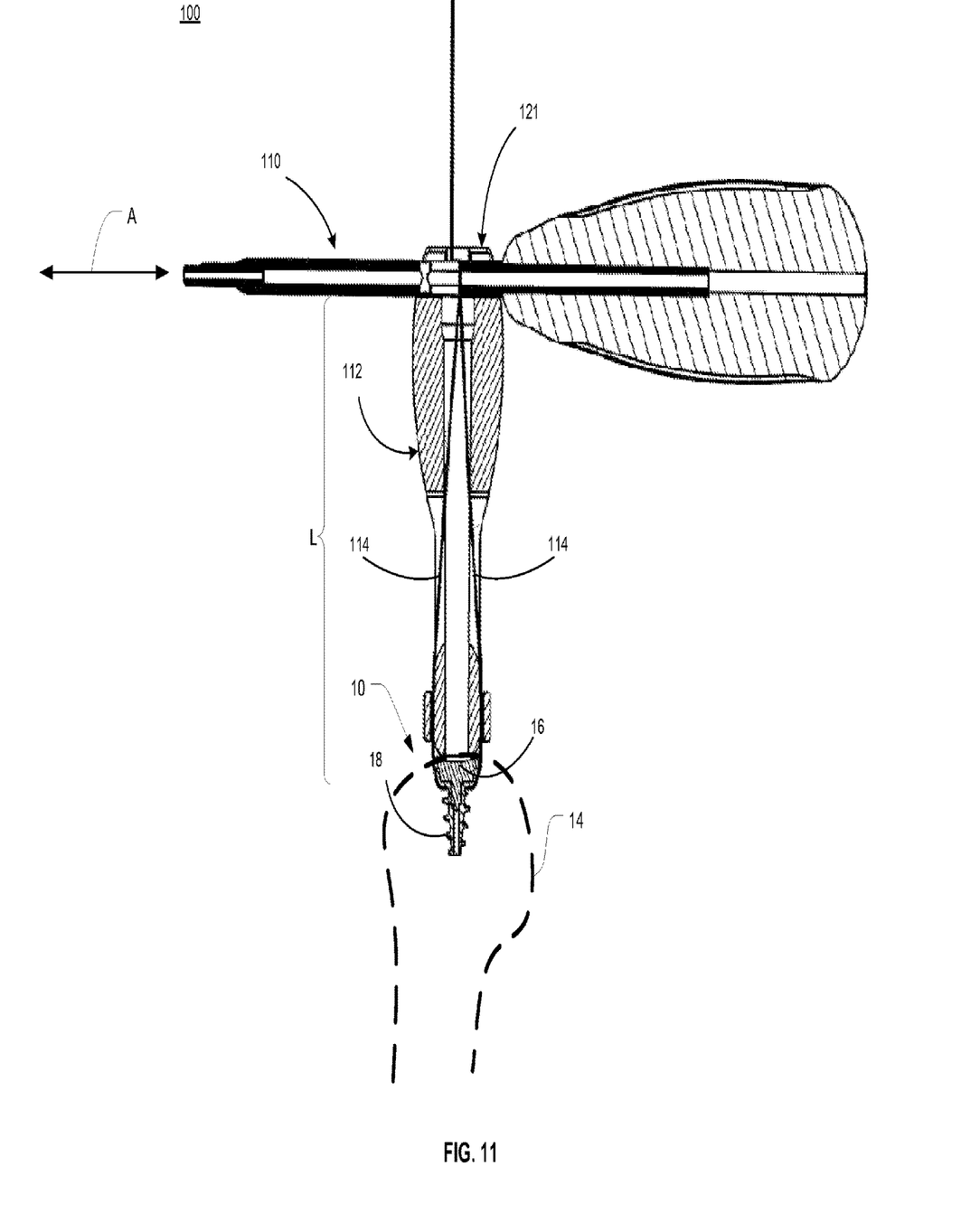
FIG. 11 generally illustrates another cross-sectional view of an implant delivery system securing an implant to an anchor consistent with the present disclosure.
Figure 12:
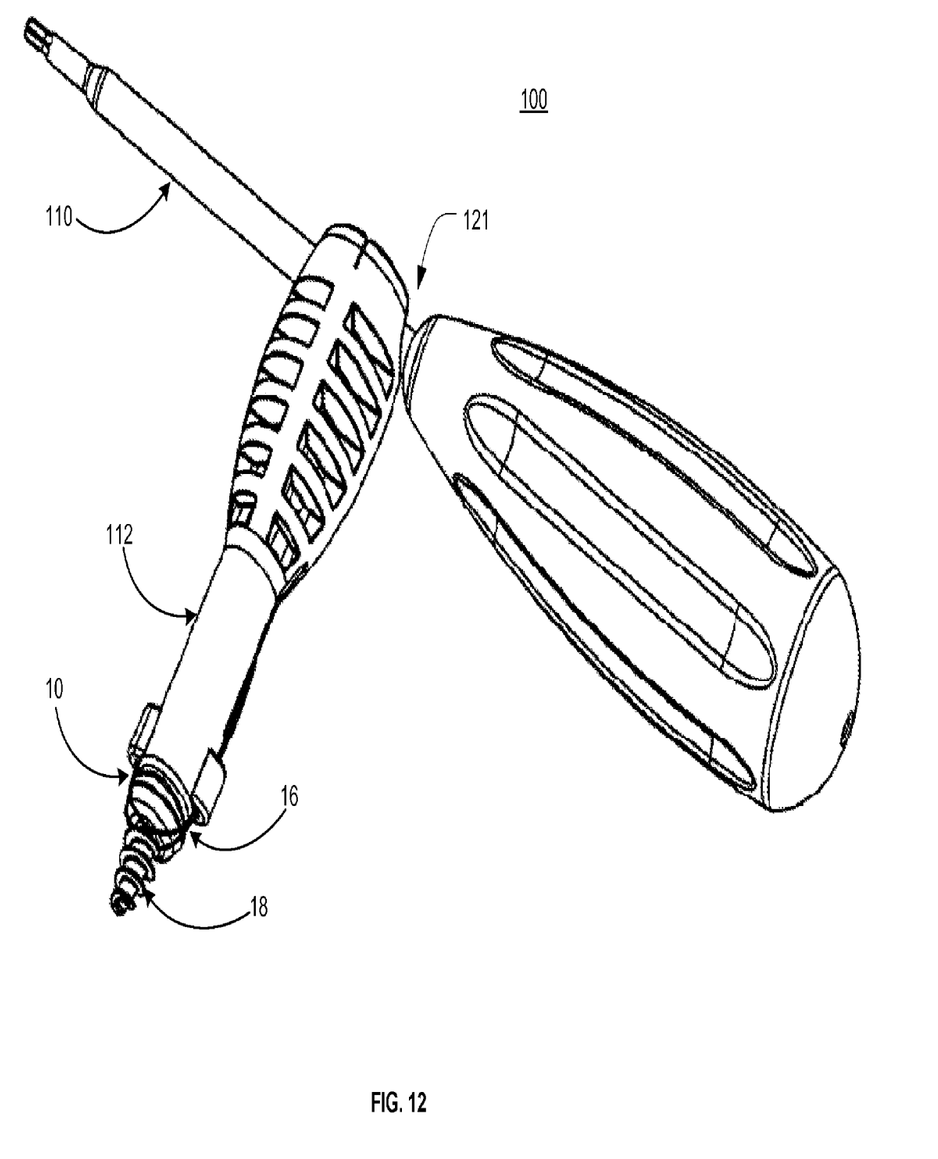
FIG. 12 generally illustrates another perspective view of an implant delivery system for securing an implant to an anchor consistent with the present disclosure.

Turning now to FIGS. 11 and 12, with the implant 16 disposed between the anchor 18 and the second end region 132b of the biasing body 112, and the driver 110 (along with the suture 114 generally secured thereto) disposed within the driver cradle 121, the surgeon may rotate the driver 110 about longitudinal axis A to reduce the length L of the suture 114 extending between the driver 110 and the contact portion 120 of the anchor 118. The reduction in the length L of the suture 114 generates a biasing force which urges the implant 16 into engagement with the anchor 18. As may be appreciated, the implant delivery system 100 generates a biasing force which is applied against the implant 16 and anchor 18 through the suture 114 only (i.e., substantially no force is applied to the surrounding bone 14 or tissue).

More specifically, because the suture 114 supports the anchor 18, rotation of the driver 110 about longitudinal axis A increases the tension on the suture 114 (and therefore the biasing force between the implant 16 and the anchor 18) in an opposite direction of the downward force being placed upon the implant 16 by the biasing body 112. Continued rotation of the driver 110 increases the biasing force between the implant 16 and the anchor 18 and, once the biasing force exceeds the required threshold to install the implant 16, the implant 16 may be successfully installed (e.g., secured) in the anchor 18. Thus, as a result of the suture 114 applying a relatively equal and opposite force to the anchor 18 and the biasing device 110 (and therefore the implant 16), the underlying bone 14 and other structures are not affected, preventing or reducing potential injury from securing the implant 16 into the anchor 18. The implant delivery system 100 therefore avoids and/or reduces any impact to the bone 14 (e.g., eliminates blunt force due to a hammer/mallet or the like), and therefore avoids and/or reduces damage to the bone 16.

Because the biasing force is not transmitted/applied into the surrounding bone 14 or tissue, the implant delivery system 100 may be used with small bones (such as, but not limited to, phalange bones and/or metatarsal bones in the foot and/or hands. Additionally, because the implant delivery system 100 is capable of generating high biasing forces without transmitting/applying the biasing force to the surrounding bone 14 or tissue, the connection between the implant body 16 and the anchor 18 (e.g., first and second fixation elements 24, 26 as discussed herein) may be stronger and more robust, thereby increasing the life expectancy of the implant system 10. Moreover, the implant delivery system 100 may deliver the biasing force uniformly to the implant 16 and be self-leveling or self-aligning, thereby reducing and/or eliminating the difficulties associated with aligning the implant 16 with respect to the anchor 18.

Once the implant 16 is secured to the anchor 18, the suture 114 may be removed from the implant system 10. For example, one or more portions of the suture 114 may be cut and the resulting pieces may be removed (e.g., pulled out) from the excision site 20. Alternatively, a first end of the suture 114 may be released and the suture 114 may be pulled through the biasing body 120 by a second end of the suture 114, resulting in the first end traveling through the shaft passageway 132c, through one of the suture passageways 136a, 136b, out one of the alignment guides 138a, 138b, around the anchor 18 and through the second of the alignment guides 138a, 138b and suture passageways 136a, 136b, and the shaft passageway 132. However, example embodiments may vary and are not limited thereto.

If the suture 114 is cut prior to removal, example embodiments may vary and may include the suture 114 having various shapes or loops. For example, the suture 114 may form a basket or loop to wrap around the anchor 18. This shape may help support the anchor 18 and may increase control over the anchor 18 prior to the suture 114 being wrapped around the driver 110. In this configuration, the loop may extend so that the loop can be severed after installation of the implant system 10.

According to one aspect, the present disclosure may feature a delivery system for securing an implant with an anchor. The delivery system may include a driver including a shaft and a biasing body. The driver may be configured to wind a portion of a suture, wherein the suture is configured to extend around a contact portion of the anchor disposed within a bone. The biasing body may have a first end region and a second end region. The first end region may include a driver cradle configured to generally retain a portion of the shaft as the driver is rotated relative to the biasing body. The second end region may be configured to engage a portion of the implant. Rotation of the driver applies a biasing force against the implant and the anchor to secure the implant with the anchor, wherein the biasing force is substantially not transmitted to the bone.

According to another aspect, the present disclosure may feature a system comprising an implant system, at least one suture, and an implant delivery system. The implant system includes an anchor configured to be secured in bone beneath a patient's articular surface, and an implant configured to be secured to the anchor. The implant is configured to replace a portion of the patient's articular surface. The suture has a first portion configured to be disposed about a portion of the anchor. The implant delivery system includes a driver including a shaft, and a biasing body having a first end region configured to engage the driver and a second end region configured to engage a portion of an implant. The driver is configured to wind a second portion of the suture while engaged against the first end region to reduce a length of the suture between the driver and the anchor and generate a biasing force urging the implant into engagement with the anchor, wherein the biasing force is substantially not transmitted to the bone.

According to yet another aspect, the present disclosure may feature a method of installing an articular surface implant in an excision site formed in a patient's bone. The method includes securing an anchor in the patient's bone within the excision site, and applying a biasing force against an implant to urge the implant into engagement with the anchor, wherein the biasing force is substantially not transmitted to the bone.

According to a further aspect, the present disclosure may feature an implant system. The implant system may include an implant body and an anchor. The implant body may include a load bearing surface having a contour substantially corresponding to a removed portion of a patient's articular surface, a bone facing surface, and a first fixation element. The anchor may be configured to be secured in bone beneath the removed portion of the patient's articular surface, and may include a second fixation element. The first and the second fixation element may be are configured to form a snap-fit connection therebetween.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A system comprising:
    an implant system including:
        an anchor configured to be secured in bone beneath a patient's articular surface, said anchor having an inner passageway therethrough; and
        an implant configured to be secured to said anchor, said implant configured to replace a portion of said patient's articular surface;
    a suture having a first portion configured to be disposed around an exterior portion of said anchor, such that said suture is spaced apart from the inner passageway; and
    an implant delivery system comprising:
        a driver including a shaft; and
        a biasing body having a first end region configured to engage said driver, a second end region configured to engage a portion of said implant;
        wherein a second portion of said suture is configured to extend from said exterior portion of said anchor to interface with said driver, such that said biasing body is disposed between said first and second portions of said suture;
        wherein said driver is configured to rotate while engaged against said first end region to reduce a length of said suture between said driver and said anchor and generate a biasing force urging said implant into engagement with said anchor, and wherein said biasing force is substantially not transmitted to said bone.

2. The system of claim 1, wherein the suture includes a cradle configured to engage a contact portion of said anchor.

3. The system of claim 2, wherein said biasing body is configured to maintain a separation angle of said cradle.

4. The system of claim 3, wherein the biasing body includes at least one suture alignment guide configured to maintain said separation angle of said cradle.

5. The system of claim 1, wherein the driver comprises a first engagement portion, said anchor comprises a second engagement portion, and wherein said first and second engagement portions are configured to be coupled with each other so as to transmit torque therebetween.

6. The system of claim 1, wherein the biasing body is self-aligning with respect to said implant as said biasing force is applied.

7. The system of claim 1, wherein said driver is configured to rotate relative to said biasing body.

8. The system of claim 7, wherein said first end region includes a driver cradle configured to generally retain a portion of said shaft as said driver is rotated relative to said biasing body.

9. The system of claim 1, wherein said suture is configured to extend from said exterior portion of said anchor through i) a suture passageway within said biasing body, and ii) an opening at the first region, so as to interface with said driver.

10. The system of claim 9, wherein said biasing body comprises one or more lateral openings to receive said suture therein.

* * * * *